United States Patent [19]  
Iwakura et al.

[11] Patent Number: 4,777,046  
[45] Date of Patent: Oct. 11, 1988

[54] SHEET-LIKE PREPARATION

[75] Inventors: Taiichiro Iwakura; Tadafumi Mizobuchi, both of Kagawa; Yukio Aouda, Tokyo, all of Japan

[73] Assignees: Nippon Kayaku Kabushiki Kaisha, Tokyo; Teikoku Seiyaku Kabushiki Kaisha, Kagawa; Kaken Pharmaceutical Co., Ltd., Tokyo, all of Japan

[21] Appl. No.: 782,417

[22] Filed: Oct. 1, 1985

[30] Foreign Application Priority Data

Oct. 4, 1984 [JP] Japan ................................ 59-207113

[51] Int. Cl.⁴ ............................................. G61K 6/00
[52] U.S. Cl. ...................................... 424/435; 424/447
[58] Field of Search ................................ 424/435, 447

[56] References Cited

U.S. PATENT DOCUMENTS 3,598,123 8/1971 Zaffaroni ............................ 424/435
4,393,080 7/1983 Pawelchak et al. .
4,569,837 2/1986 Suzuki et al. ....................... 424/435
4,572,832 2/1986 Kigasawa et al. .................. 424/435
4,680,323 7/1987 Lowry ................................ 424/435

OTHER PUBLICATIONS

Chemical Abstracts 88: 19948h, Hydrophilic Plasters (identifies Japanese Patent Application No. 77-31,926).
Patent Abstracts of Japan, vol. 9, No. 45 (identifies Japanese Patent Application No. 59-186913).
European Patent Application No. 0 050 480.

Primary Examiner—Thurman K. Page  
Assistant Examiner—L. R. Horne  
Attorney, Agent, or Firm—Banner, Birch, McKie & Beckett

[57] ABSTRACT

A sheet-like preparation comprising a composition comprising (a) a drug, (b) gelatin or agar, (c) gluten, (d) a carboxyvinyl polymer, (e) a polyhydriic alcohol, (f) a gum and (g) wax as its essential constituents, and water in an amount of 0 to 30 w/w % based on the total weight of the essential constituents, and a sheet-like support which supports thereon said composition.

The sheet-like preparation of this invention is useful, for example, as a preparation for oral cavity administration.

6 Claims, No Drawings

SHEET-LIKE PREPARATION

BACKGROUND OF THE INVENTION

1. Field of the Invention

This invention relates to a sheet-like preparation for oral cavity administration. More particularly, this invention relates to a sheet-like preparation for oral cavity administration, comprising a composition comprising (a) a drug, (b) gelatin or agar, (c) gluten, (d) a carboxyvinyl polymer, (e) a polyhydric alcohol, (f) a gum and (g) a wax as its essential constituents, and water in an amount of 0 to 30 w/w % based on the total weight of the essential constituents, and a sheet-like support which supports thereon said composition.

2. Description of the Prior Art

As preparations for oral cavity administration, there have herefore known oral cavity tablets, sublingual tablets, etc.

However, like ordinary tablets for internal use, these tablets have a considerable volume and are hard, so that they are apt to move in the oral cavity. Since they are very liable to be swallowed as in the case of oral administration, they are difficult to keep in the oral cavity for a long time. Therefore, when a drug is administered through a mucosa in the form of tablet, it is difficult to attain pharmaceutical usefulness such as control of the release and absorption rates of the drug, long-time duration of the effect of the drug, and the like.

SUMMARY OF THE INVENTION

Accordingly, the present inventors have conducted various researches on sustained-release preparations which can be kept and adhered in the oral cavity for a long time, and have found the following fact. When in the oral cavity is stuck a preparation obtained by homogeneously kneading a composition comprising (a) a drug, (b) gelatin or agar, (c) gluten, (d) a carboxyvinyl polymer, (e) a polyhydric alcohol, (f) a gum, (g) a wax, and water, spreading the kneaded composition on a sheet-like support, and then drying the composition so that its water content becomes 0 to 30 w/w % based on the total weight of the above-mentioned constituents (a) to (g), the preparation absorbs saliva in the oral cavity to be swollen, so that it is increased in adhesive strength on its surface and is enabled to be kept in the inner wall of the oral cavity and the gingiva for a long time, and that the drug is gradually released from the swollen preparation matrix at a controlled speed.

Tis invention has been accomplished on the basis of the above finding.

DETAILED DESCRIPTION OF THE INVENTION

The drug used in this invention is not critical. For example, drugs expected to exert local effects include prostaglandins, non-steroidal anti-inflammatory and analgesic agents (e.g., indomethacin, diclofenac sodium, ibuprofen, etc.), local anesthetics (e.g., lidocaine, tetracaine, procaine, etc.), antibiotics for pyorrhea alveolaris (e.g., tetracycline, amplicillin, rifampicin, etc.), steroid agent (triamcinolone acetonide), and the like. Drugs expected to exert systemic effects include cardiovascular agents (e.g., nitroglycerin, isosorbide dinitrate, propranolol, dipyridamole, nifedipine, etc.), drug for diabets (insulin), central nerve depressors (chloral hydrate, methylpentynol, etc.), antiallergics (e.g., tripelennamine, cyproheptadine, etc.), and the like.

The gluten used in this invention is one which is widely used in foods and the like, and is a mixture of proteins obtained from wheat. The carboxyvinyl polymer includes, for example, acid type ones such as polyacrylic acids, partially crosslinked polyacrylic acids (e.g., carbopol etc.), and the like.

The polyhydric alcohol includes, for example, glycerol, propylene glycol, polyethylene glycol, 1,3-butanediol, sorbitol, etc. which are used, for example, in poultices and the like.

The gum includes vegetable gums such as natural rubber, guar gum, natural chicle, xanthan gum, gugm arabic, tragacanth gum, karaya gum, locust bean gum and the like, ester gum (glycerol ester of rosin), etc. These may be used alone or in combination, and may be incorporated with compounding agents such as polyisobutylene and the like. The wax includes beeswax, carnauba wax, lanoline, microcrystalline wax, etc.

The proportions of the essential constituents to be used in the preparation of this invention are as follows: Based on the total weight of the essential constituents, the proportion of (a) the drug is 0.01 to 50 w/w %; that of (b) gelatin or agar is 1 to 70 w/w %, preferably 1 to 50 w/w %, more preferably 1 to 40 w/w %, that of (c) gluten is 1 to 70 w/w %, preferably 5 to 50 w/w %, more preferably 5 to 35 w/w %; that of (d) the carboxyvinyl polymer is 1 to 50 w/w %, preferably 5 to 40 w/w %, more preferably 5 to 30 w/w %; that of (f) the gum is 1 to 70 w/w %, preferably 5 to 50 w/w %, more preferably 5 to 35 w/w %; that of (g) the wax is 1 to 30 w/w %, preferably 1 to 20 w/w %, more preferably 2 to 15 w/w %; and that of (e) the polyhydric alcohol is 1 to 50 w/w %, preferably 10 to 40 w/w %, more preferably 15 to 35 w/w %.

The preparation of this invention may be incorporated with base components usually usable in conventional poultices, ointments and the like, for example, purified water, cellulose derivatives such as methyl cellulose, ethyl cellulose, propyl cellulose, ethylmethyl cellulose, hydroxyethyl cellulose, hydroxypropyl cellulose, carboxymethyl cellulose and the like, talc, sodium polyacrylate, polyvinyl pyrrolidone, etc. The incorporating proportions of the base components are as follows: Based on the total weight of the constituents of the preparation of this invention (the constituents (a) to (g)), the incorporating proportion of water is 0 to 30 w/w %, preferably 0.5 to 25 w/w %, more preferably 1 to 20 w/w %; and that of the other components is 0 to 30 w/w %, preferably 0.1 to 20 w/w %, more preferably 0.5 to 15 w/w %.

Further, the preparation of this invention may be incorporated with a suitable amount of antiseptics and seasoning agents such as methyl ester and propyl ester of p-oxybenzoic acid, and the like.

A more preferable embodiment of the preparation of this invention is, for example, as follows: The proportion of the drug to be used is 0.1 to 10 w/w %, and in the case of prostaglandins the dosage of which may be small, it is 0.1 to 0.5 w/w %; that of gelatin or agar is 2 to 10 w/w %, preferably 2 to 7 w/w %; that of gluten is 15 to 45 w/w %, preferably 25 to 35 w/w %; that of the carboxyvinyl polymer is 10 to 40 w/w %, preferably 15 to 25 w/w %; that of polyhydric alcohol is 10 to 40 w/w %, preferably 20 to 30 w/w %; that of the gum is 6 to 20 w/w %, preferably 8 to 15 w/w %; that of the wax is 4 to 15 w/w %, preferably 5 to 10 w/w %; based on the total weight of these constituents, the proportion of talc is 3 to 10 w/w %, that of sodium polyacrylate is 2 to 15 w/w %, preferably 3 to 10 w/w %, that of polyisobutylene is 0.5 to 10 w/w %, preferably 1 to 5 w/w %, and that of water (by Karl Fisher's method) is 0.5 to 20 w/w %, preferably 1 to 15 w/w %, and in some preparations, 2 to 5 w/w %; and the pH of the preparation is 7 to 9.

The preparation of this invention is produced, for example, in the following manner.

Gelatin or agar, gluten, the carboxylvinyl polymer, the gum and the wax are added to purified water, and the resulting mixture is stirred and kneaded with heating at 70° to 90° C. for 0.5 to 10 hours, preferably 1 to 5 hours to obtain a pasty composition. Next, a homogeneous solution or suspension of the drug in the polyhydric alcohol is added to the pasty composition. The mixture thus obtained is homogeneously kneaded and stirred for 0.5 to 10 hours, preferably 1 to 5 hours, thereafter spread and coated on a suitable support while compressing, and then dried at 10° to 50° C. for 10 hours to 2 days usually until the water content of the base becomes 0 to 30 w/w % based on the total amount of the constituents (a) to (g) of the preparation of this invention, whereby there can be obtained an excellent preparation for sticking to mucosal of the oral cavity and the gingiva. Here, the amount of purified water initially used is 0.5 to 5 times, preferably 1 to 4 times the total amount of the above-mentioned constituents (a) to (g). The supports includes films of polyolefins such as polyethylene, polypropylene and the like, polyesters and polyvinyl chlorides; nonwoven fabric; etc.

When adjustment of the pH is necessary, it is sufficient that an alkaline substance such as sodium carbonate or the like or an acidic substance such as hydrochloric acid or the like is added to the pasty composition after or before the addition of the drug.

The excellence of the preparation of this invention is shown below by way of Experiment Examples.

EXPERIMENT EXAMPLE 1

Adhesive property test (1) Sample

The preparation obtained in Example 4 shown later was used as a sample (Sample A). On the other hand, a preparation produced in the same manner as in Example 4 except for omission of the carboxyvinyl polymer and microcrystalline wax is used as a reference sample (Sample B).

(2) Test method

Ten pieces of each sample were stuck in a circle to 10 places on the inner surface of an 1-liter beaker containing 800 ml of 0.1M phosphate buffer (pH 6.2) heated to 37°±0.5°. The temperature of the buffer was maintained at 37°±0.5° C., and while stirring the buffer at 100 r.p.m. by means of a magnetic stirrer, peeling-off of the test pieces with the lapse of time was observed until after 5 hours.

(3) Result

The results obtained are shown in Table 1.

TABLE 1

| Sample | | Time (h) | | | | | | Total number of test pieces which peeled off |
|---|---|---|---|---|---|---|---|---|
| | | 0.5 | 1 | 2 | 3 | 4 | 5 | |
| A | Run 1 | 0 | 0 | 0 | 0 | 1 | 1 | 2 |
| | 2 | 0 | 0 | 0 | 1 | 1 | 1 | 2 |
| | Average | 0 | 0 | 0 | 0.5 | 1 | 1 | 2.5 |
| B | 1 | 1 | 1 | 1 | 3 | 1 | 1 | 8 |
| (Reference) | 2 | 0 | 1 | 2 | 2 | 1 | 2 | 8 |
| | Average | 0.5 | 1 | 1.5 | 2.5 | 1 | 1.5 | 8 |

As is evident from this table, only 2.5 of 10 test pieces of the sample of this invention peeled off, whereas 8 of 10 test pieces of the reference sample peeled off. From this fact, it can be seen that the adhesive strength of the preparation of this invention is excellent.

EXPERIMENT EXAMPLE 2

Sticking test (1) Sample

The preparation obtained in Example 1 (shown later) was used as a sample.

(2) Experiment method

The sample was stuck to the mucosae of gingiva of two volunteers before bedtime, and its adhesive property was examined.

(3) Results

Both of the test pieces stuck to the two volunteers did not peel off until the hour of rising (after 8 hours) and adhered tightly.

EXPERIMENT EXAMPLE 3

Test for remaining of drug (1) Sample

The preparation obtained in Example 1 was used as a sample.

(2) Experiment method

The sample was stuck to 4 male volunteers (24 to 30 years old). It was taken out at regular intervals and the drug in the sample was quantitatively determined.

(3) Results

The results obtained are shown in Table 2.

TABLE 2

| Subject | Sticking time | | | | |
|---|---|---|---|---|---|
| | 0.5 | 1 | 2 | 3 | 4 |
| A | 93.9 | 92.2 | 89.1 | 82.3 | 69.2 |
| B | 79.7 | 84.1 | 71.5 | 66.8 | 58.1 |
| C | 90.0 | 80.1 | 74.4 | 62.1 | 62.7 |
| D | 96.7 | 84.8 | 80.5 | 70.2 | 64.4 |

From this table, it can be seen that since 50% or more of the drug remains in the patch of this invention even 4 hours after the beginning of the test, said patch is excellent as a sustained-release preparation.

As is evident from above Experiment Examples, the preparation of this invention is good in adhesion and sustained-release in the oral cavity and hence is excellent as a preparation for the oral cavity.

That is to say, the preparation of this invention absorbs saliva to be swollen, resulting in an increase of its adhesive strength, and therefore it can be stuck to a sticking place for 8 hours or more, if necesary, about 24 hours, and can be expected to release the drug continuously during a sticking period. The present preparation is good in the degree of utilization of drug as compared with conventional patches, and it has a suitable flexibility and its thickness can be properly adjusted to about 10 to 1,000 μm, and therefore it can give a good feeling of use which is suitable for the drug.

The present invention is illustrated in more detail below referring to the following Examples. However, the invention is not to be limited thereto.

EXAMPLE 1

With 15 g of gelatin were mixed 10 g of gluten, 10 g of carboxyvinyl polymer, 15 g of guar gum and 5 g of lanolin, after which 100 g of purified water was added, and the resulting mixture was stirred and kneaded with heating at 75° to be made pasty. Subsequently, 10 g of sodium dichlofenac dissolved in 35 g of sorbitol was added, and the resulting mixture was again stirred and kneaded, and then deaerated. The pasty composition thus obtained was spread on a polyvinyl chloride film while compressing in a proportion of 500 g/m² and then dried in a thermostated room at 30° C. until its water content became 10%. Then, the film was cut into a predetermined size (3 cm×1 cm) to obtain the preparation of this invention.

EXAMPLE 2

Together with 250 g of purified water, 10 g of agar, 30 g of gluten, 25 g of carboxyvinyl polymer, 10 g of karaya gum and 10 g of lanolin were homogeneously kneaded to obtain a pasty composition. Subsequently, a suspension of 10 g of indomethacin in 50 g of glycerol was added. Thereafter, operations were performed according to Example 1, except that the water content was changed to 20 %, to obtain the preparation of this invention.

EXAMPLE 3

Together with 200 g of purified water, 30 g of gelatin, 20 g of gluten, 20 g of carboxyvinyl polymer, 10 g of guar gum and 5 g of microcrystalline wax were homogeneously kneaded to obtain a pasty composition. Subsequently, a suspension of 10 g of indomethacin in 40 g of sorbitol was added. Thereafter, operations were performed in the same manner as in Example 1, except that the water content was changed to 15%, to obtain the preparation of this invention.

EXAMPLE 4

With 5 g of natural rubber were mixed 20 g of ester gum, 5 g of polyisobutylene, 10 g of agar, 15 g of talc, 50 g of carboxyvinyl polymer, 75 g of gluten, 15 g of sodium polyacrylate and 20 g of microcrystalline wax, after which 700 g of purified water was added, and the resulting mixture was stirred and kneaded with heating at 80° C. to be made pasty. Subsequently, a solution of 0.8 g of prostaglandin $F_2 \alpha$ in 70 g of polyethylene glycol was added, and the resulting mixture was again stirred, adjusted to pH 7 to 9, and then unaerated. The pasty composition thus obtained was spread on a polypropylene film while compressing in a proportion of 500 g/m², and then dried in a thermostated room at 30° C. until its water content became 5%. Then, the film was cut into a predetermined size (3 cm×1 cm) to obtain the preparation of this invention.

What is claimed is:

1. A pharmaceutical preparation in the form of a film or sheet comprising a composition of (a) 0.01 to 50 w/w % for the drug, (b) 1 to 70 w/w % of gelatin or agar, (c) 1 to 70 w/w % gluten, (d) 1 to 50 w/w % of carboxyvinyl polymer, (e) 1 to 50 w/w % of a polyhydric alcohol, (f) 1 to 70 w/w % of a gum and (g) 1 to 30 w/w % of a wax and 0 to 30 w/w % of water, in which said film or sheet supports the composition thereon.

2. A pharmaceutical preparation in the form of a film or sheet according to claim 1, wherein the proportions of the individual constituents based on the total weight of the essential constituents are 0.1 to 20 w/w % for the drug, 1 to 40 w/w % for gelatin or agar, 5 to 50 w/w % for gluten, 5 to 30 w/w % for the carboxyvinyl polymer, 10 to 40 w/w % for the polyhydric alcohol, 5 to 35 w/w % for the gum, 2 to 15 w/w % for the wax, and 0.5 to 20 w/w % for water.

3. A pharmaceutical preparation in the form of a film or sheet according to claim 1, wherein the proportions of the individual constituents based on the total weight of the essential constituents are 0.1 to 10 w/w % for the drug, 2 to 10 w/w % for gelatin or agar, 15 to 45 w/w % for gluten, 10 to 40 w/w % for carboxyvinyl polymer, 15 to 35 w/w % for the polyhydric alcohol, 6 to 20 w/w % for the gum, 4 to 15 w/w % for the wax, and 0.5 to 15 w/w % for water.

4. A pharmaceutical preparation in the form of a film or sheet according to claim 1, wherein the material for the support is a polyolefin, a polyester or a polyvinyl chloride.

5. A pharmaceutical preparation in the form of a film or sheet comprising a composition comprising (a) 0.1 to 10 w/w % of a drug, (b) 2 to 7 w/w % of gelatin or agar, (c) 25 to 35 w/w % of gluten, (d) 15 to 25 w/w % of a carboxyvinyl polymer, (e) 20 to 30 w/w % of a polyhydric alcohol, (f) 8 to 15 w/w % of a gum, (g) 5 to 10 w/w % of a wax, and talc, sodium polyacrylate, polyisobutylene and water in amounts of 3 to 10 w/w %, 3 to 10 w/w %, 1 to 5 w/w % and 1 to 15 w/w %, respectively, based on the total weight of the above mentioned constituents (a) to (g), and a support in the form of a film or sheet which supports thereon said composition.

6. A pharmaceutical preparation in the form of a film or sheet according to claim 1, wherein the drug is prostaglandin and its amount is 0.1 to 0.5 w/w %.

* * * * *